(12) United States Patent
Podolski et al.

(10) Patent No.: US 9,914,696 B2
(45) Date of Patent: Mar. 13, 2018

(54) CLOMIPHENE SYNTHESIS USING A SINGLE SOLVENT

(71) Applicant: REPROS THERAPEUTICS INC., The Woodlands, TX (US)

(72) Inventors: Joseph S. Podolski, The Woodlands, TX (US); Kuang Hsu, The Woodlands, TX (US)

(73) Assignee: Repros Therapeutics Inc., The Woodlands, TX (US)

( * ) Notice: Subject to any disclaimer, the term of this patent is extended or adjusted under 35 U.S.C. 154(b) by 0 days.

(21) Appl. No.: 15/123,577

(22) PCT Filed: Mar. 9, 2015

(86) PCT No.: PCT/US2015/019493
§ 371 (c)(1),
(2) Date: Sep. 2, 2016

(87) PCT Pub. No.: WO2015/138340
PCT Pub. Date: Sep. 17, 2015

(65) Prior Publication Data
US 2017/0073302 A1    Mar. 16, 2017

Related U.S. Application Data

(60) Provisional application No. 61/951,316, filed on Mar. 11, 2014.

(51) Int. Cl.
| | | |
|---|---|---|
| C07C 213/08 | (2006.01) | |
| C07C 213/10 | (2006.01) | |
| C07C 59/265 | (2006.01) | |
| C07C 51/41 | (2006.01) | |

(52) U.S. Cl.
CPC .......... *C07C 213/08* (2013.01); *C07C 51/412* (2013.01); *C07C 59/265* (2013.01); *C07C 213/10* (2013.01); *C07B 2200/09* (2013.01)

(58) Field of Classification Search
None
See application file for complete search history.

(56) References Cited

U.S. PATENT DOCUMENTS

| | | | | |
|---|---|---|---|---|
| 2,914,563 A | * | 11/1959 | Allen ................. | C07D 295/088 544/174 |
| 3,848,030 A | * | 11/1974 | Viterbo ............... | C07F 9/65744 546/347 |
| 5,681,863 A | | 10/1997 | Bitonti et al. | |

FOREIGN PATENT DOCUMENTS

| | | | | |
|---|---|---|---|---|
| CN | 103351304 | * | 10/2013 | .......... C07C 217/18 |
| CN | 103351304 A | | 10/2013 | |

OTHER PUBLICATIONS

CN103351304 Derwent Abstract 2013.*
(Continued)

*Primary Examiner* — Clinton Brooks
(74) *Attorney, Agent, or Firm* — Morgan Lewis & Bockius, LLP

(57) ABSTRACT

The present invention provides a one-pot method for synthesizing clomiphene (a mixture of the isomers cis-clomiphene and trans-clomiphene) utilizing a single solvent. In a preferred embodiment, the single solvent is dichloromethane (DCM, also known as methylene chloride). The present invention provides an improved method for synthesizing clomiphene and purifying clomiphene isomers.

16 Claims, 3 Drawing Sheets

(56) References Cited

OTHER PUBLICATIONS

Rao et al., "Synthesis of carbon-14 labeled clomiphene", J Label Compd Radiopharm, vol. 22, pp. 245-255 (1985) (Abstract).
International Search Report for PCT/US2015/019493 dated Jun. 3, 2015.
Written Opinion for PCT/US2015/019493 dated Jun. 3, 2015.

* cited by examiner

7

8
Clomiphene
~1.8:1 E:Z mixture

CLOMIPHENE SYNTHESIS USING A SINGLE SOLVENT

CROSS-REFERENCE TO RELATED APPLICATIONS

This application claims the benefit of U.S. Provisional Application No. 61/951,316, filed Mar. 11, 2014, the contents of which are incorporated herein by reference.

FIELD OF THE INVENTION

The present invention relates to methods for synthesizing clomiphene and purifying the trans-isomer of clomiphene.

BACKGROUND

Clomiphene is a selective estrogen receptor modulator related to tamoxifen. Clomiphene is a mixture of two geometric isomers, cis-clomiphene (or zuclomiphene) and trans-clomiphene, (or enclomiphene). Clomiphene is currently approved as a mixture of both cis- and trans-isomers, the cis-isomer being present as about 30% to 50% (Merck Manual) for the induction of ovulation in anovulatory women.

Methods for synthesizing clomiphene are known in the art. For example, U.S. Pat. No. 2,914,563, the contents of which are hereby incorporated by reference, describes the preparation of clomiphene (see Example 3 in particular). U.S. Pat. No. 3,848,030, the contents of which are hereby incorporated by reference, describes a method to separate the cis- and trans-isomers of clomiphene (see Examples 31 and 32 in particular).

Current methods for preparing clomiphene require the isolation of intermediates and exchange of solvents making the process difficult to streamline. Large scale production of clomiphene and purification of the trans-isomer of clomiphene would be greatly improved if clomiphene synthesis could be accomplished using a single solvent and without the need to isolate intermediates.

SUMMARY

The present invention provides a one-pot method for synthesizing clomiphene (a mixture of the isomers cis-clomiphene and trans-clomiphene) utilizing a single solvent. In a preferred embodiment, the single solvent is dichloromethane (DCM, also known as methylene chloride). In one aspect, the method comprises dissolving 1-{4-[2-(Diethylamino)ethoxy]phenyl}-1,2-diphenylethanol in a solvent (e.g. DCM) and (i) dehydrating 1-{4-[2-(Diethylamino)ethoxy]phenyl}-1,2-diphenylethanol using a mineral acid to produce a 2-{4-[(Z)-1,2-diphenylvinyl]plenoxy}-N,N-diethylethanaminium salt and thereafter (ii) chlorinating the 2-{4-[(Z)-1,2-diphenylvinyl]phenoxy}-N,N-diethylethanaminium salt with a chlorinating agent to form clomiphene, a mixture of trans- and cis-clomiphene isomers. Both steps are accomplished in a single solvent (e.g. dichloromethane), with no isolation of chemical intermediates or change of solvent required. Once the chlorination reaction has proceeded to completion, the reaction is preferably quenched with saturated aqueous sodium bicarbonate solution or the like, after which the phases are separated and the organic layer (containing clomiphene) retained for storage or further processing.

Suitable solvents for the dehydration and chlorination steps are solvents in which 1-{4-[2-(Diethylamino)ethoxy]phenyl}-1,2-diphenylethanol is soluble and which have little or no miscibility with water. Non-limiting examples of solvents for use according to the methods described herein include chloroform, diethyl ether, ethyl ester, ethyl acetate, dichloromethane and the like. In a particularly preferred embodiment, the solvent is DCM.

Once a solvent is chosen, an acid that is compatible with the solvent is used for the dehydration step. Non-limiting examples of suitable acids include without limitation mineral acids such as hydrochloric acid, hydrobromic acid, p-toluenesulfonic acid, phosphoric acid and sulfuric acid. In a preferred embodiment, the acid is sulfuric acid. In a particularly preferred embodiment, the solvent is DCM and the acid is sulfuric acid. When sulfuric acid is used for the dehydration step, the internal temperature of the solution is preferably maintained at about 0° C. during the addition of the acid after which the mixture is stirred for one hour at ambient temperature. The reaction is generally complete after about one hour.

The water that is produced by the dehydration reaction should be removed prior to the chlorination step by any suitable method including without limitation, anhydrous salts such as magnesium sulfate, sodium sulfate or the like, molecular sieve, or washing with brine. In a preferred embodiment, at least 80%, 90%, 95%, or 99% of the water produced by the dehydration reaction is removed prior to the chlorination step.

Suitable chlorination agents include, without limitation, N-chlorosuccinimide (NCS). When N-chlorosuccinimide is employed to effect the chlorination, an initial slight excess (e.g. ~1.05 equivalents) of NCS is added and the reaction is allowed to proceed for at least 12 hours after which the degree of completion of the reaction is assessed, for example by high performance liquid chromatography (HPLC). If necessary, additional NCS may be added and the reaction allowed to proceed for additional time (e.g. 4 hours) and the degree of reaction completion against tested by HPLC and so on.

In a preferred embodiment, clomiphene produced according to the above-described procedure is converted to the free base (e.g. using NaOH, sodium bicarbonate and the like) and then loaded onto a chromatography column in the same solvent employed in the dehydration and chlorination steps in order to separate the cis- and trans-isomers. In embodiments, batch high pressure chromatography or moving bed chromatographic methods are employed to separate the isomers.

In a related aspect, the chromatography column is eluted using a solvent suitable for crystallizing trans-clomiphene and recrystallizing the trans-clomiphene following elution from the column.

In other embodiments, clomiphene produced according to the above-described procedure is reacted with racemic binaphthyl-phosphoric acid (BPA) and the trans-clomiphene-BPA salt isolated. In related embodiments, trans-clomiphene is thereafter converted to the free base form and treated with citric acid to form trans-clomiphene citrate.

DETAILED DESCRIPTION

Figure 1:
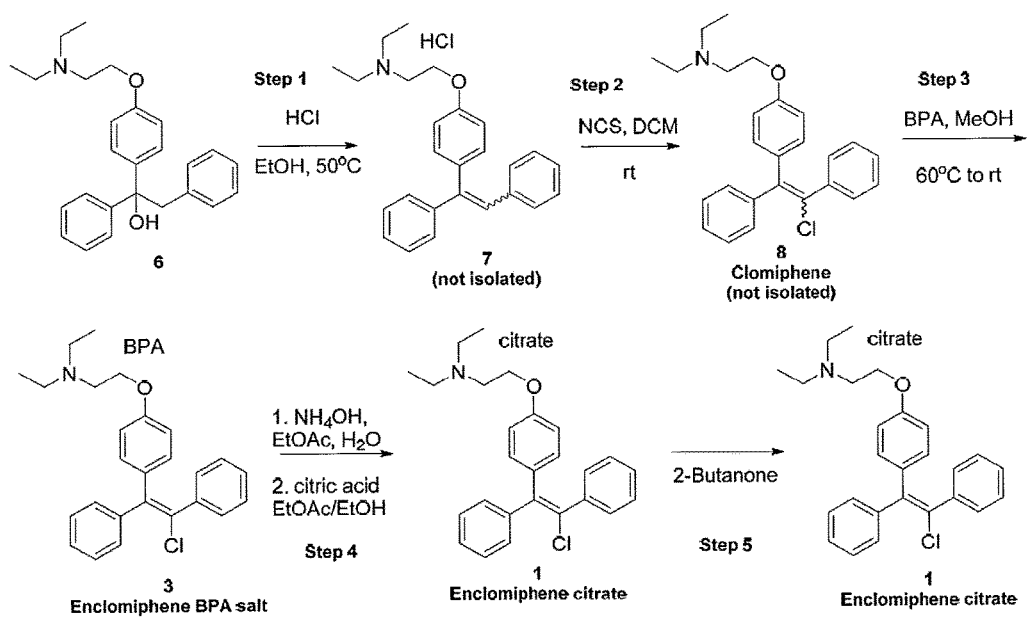
FIG. 1 shows a synthesis route to trans-clomiphene.
Figure 2:
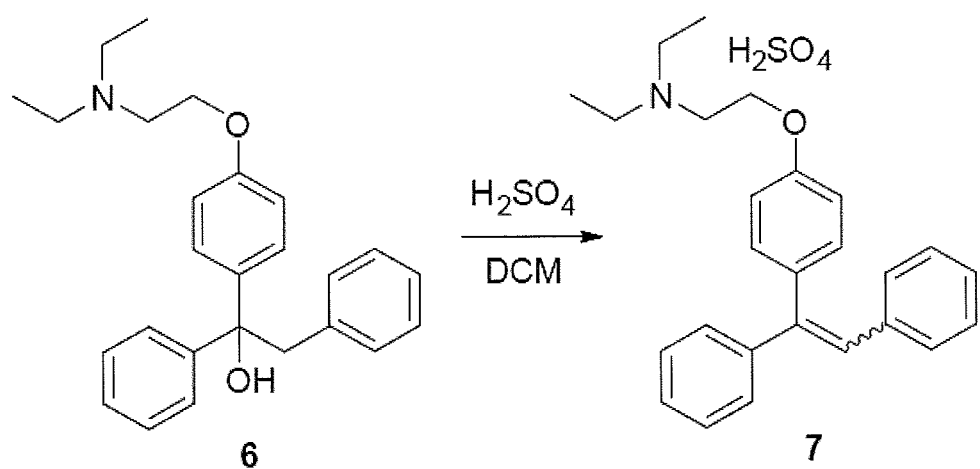
FIG. 2 shows an alternate method for the dehydration step in FIG. 1.
Figure 3:
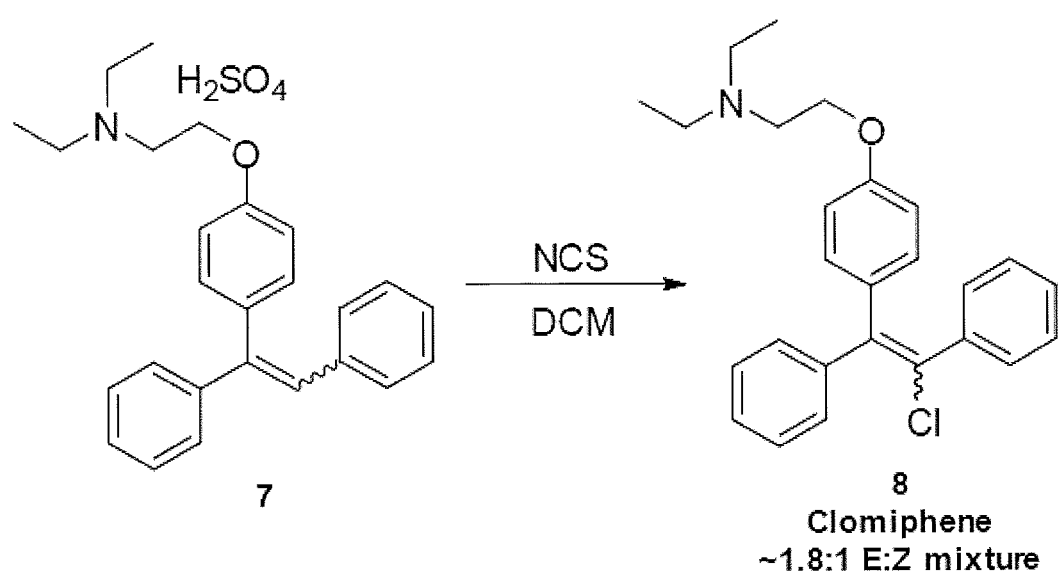
FIG. 3 shows the chlorination step including the ratio of isomers obtained.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

It is to be understood that any ranges, ratios and ranges of ratios that can be formed by any of the numbers or data present herein represent further embodiments of the present invention. This includes ranges that can be formed that do or do not include a finite upper and/or lower boundary. Accordingly, the skilled person will appreciate that many such ratios, ranges and ranges of ratios can be unambiguously derived from the data and numbers presented herein and all represent embodiments of the invention.

Before the present compounds, compositions and methods are disclosed and described, it is to be understood that the terminology used herein is for the purpose of describing particular embodiments only and is not intended to be limiting. It must be noted that, as used in the present specification and the appended claims, the singular forms "a," "an" and "the" include plural referents unless the context clearly dictates otherwise.

The term "dichloromethane" (or methylene chloride) is an organic compound with the formula $CH_2Cl_2$.

Trans-clomiphene refers to the trans-isomer of clomiphene with the chemical name trans-2-(p-(2-chloro-1,2-diphenylvinyl)phenoxy)triethylamine (or trans-2-[4-(2-chloro-1,2-diphenylethenyl)phenoxy]-N,N-diethylethanamine). Trans-clomiphene is a selective estrogen receptor modulator (SERM) which is believed to interfere at a hypothalamic level with steroid feedback inhibition of gonadotropin secretion thereby increasing the release of FSH and LH.

The following Examples are meant to be illustrative of the invention and are not intended to limit the scope of the invention as set out is the appended claims.

Example 1

Preparation of trans-clomiphene citrate from 1-{4-[2-(Diethylamino)ethoxy]phenyl}-1,2-diphenylethanol Dehydration 1-{4-[2-(Diethylamino)ethoxy]phenyl}-1,2-diphenylethanol (6) dissolved in ethanol containing an excess of hydrogen chloride was refluxed 3 hours at 50° C. The solvent and excess hydrogen chloride were removed under vacuum and the residue was dissolved in dichloromethane. 2-{4-[(Z)-1,2-diphenylvinyl]phenoxy}-N,N-diethylethanaminium hydrogen chloride (7) was obtained.

Chlorination

The hydrochloride salt (7) solution obtained above was treated with 1.05 equivalents of N-chlorosuccinimide and stirred at room temperature for about 20 hours. Completion of the reaction was confirmed by HPLC. The hydrochloride salt was converted to the free base by addition of saturated aqueous bicarbonate solution. The mixture was stirred at room temperature for 30 minutes after which the phases were separated and the organic phase was evaporated in vacuo. 2-{4-[2-chloro-1,2-diphenylvinyl]phenoxy}-N,N-diethylethanamine (clomiphene ~1.8:1 E:Z mixture) (8) was obtained.

Separation of Clomiphene Isomers

Clomiphene (8) obtained above is dissolved in methanol and racemic binaphthyl-phosphoric acid (BPA) is added under stirring. When the precipitate begins separating from the solution, stirring is stopped and the mixture is allowed to settle at room temperature for 2 hours. The precipitate is filtered, washed with methanol and ether and dried. Trans-clomiphene-BPA salt (3) is obtained.

The enclomiphene-BPA salt (3) obtained above is extracted with ethyl acetate and $NH_3$ solution. To the organic solution washed with water and dried, citric acid dissolved in ethanol is added. The solution is allowed to settle for about one hour at room temperature; the precipitate is then filtered and dried under vacuum. The obtained precipitate, trans-clomiphene citrate (1) is dissolved in 2-butanone for storage.

Example 2

Synthesis of Clomiphene Using a Single Solvent

Step 1—Dehydration of 1-{4-[2-(Diethylamino)ethoxy]phenyl}-1,2-diphenylethanol to form 2-{4-[(Z)-1,2-diphenylvinyl]phenoxy}-N,N-diethylethanaminium hydrogen sulfate (7)

The synthesis route described in Example 1 utilized HCl for the dehydration step and utilized ethanol at 50° C. as the solvent. Sulfuric acid was investigated as an alternative to HCl for the dehydration step (as described in Example 1) in part due to the more favorable corrosion profile of sulfuric acid. Dichloromethane (methylene chloride) was investigated as an alternative solvent for the dehydration step as this would render removal of the ethanol solvent prior to the chlorination step unnecessary.

A 100 mL 3-neck round bottom flask, fitted with a temperature probe and a stir bar, was charged with 1-{4-[2-(Diethylamino)ethoxy]phenyl}-1,2-diphenylethanol (6) (6.60 g, 16.9 mmol) and 66 mL ($1\times10^3$ mmol) of methylene chloride to give a yellow solution which was cooled in an ice bath to 0° C. Concentrated sulfuric acid ($H_2SO_4$, 0.96 mL, 18.1 mmol) was added at a rate such that the internal temperature did not exceed 5° C. Upon completion of the addition, the mixture was allowed to stir one hour at ambient temperature. Completion of the reaction was confirmed by high performance liquid chromatography (HPLC). The reaction resulted in 7.96 grams of 2-{4-[(Z)-1,2-diphenylvinyl]phenoxy}-N,N-diethylethanaminium hydrogen sulfate (7), a yield of 100%. Thus, sulfuric acid was demonstrated to be a suitable acid for the dehydration step.

HPLC Conditions (Dehydration Step):
Sample preparation: Dissolve 1 mg/ml in methanol
Agilent 1100 HPLC
Zorbax Eclipse XDB-C18 50×4.6 mm 1.8 μm column
Solvent A—Water (0.1% TFA)
Solvent B—Acetonitrile (0.07% TFA)
Flow rate—1.50 mL/min
Injection volume—5 μL
Gradient—5 min 95% A to 95% B; 1 min hold; 1 min recycle; 30 sec hold
UV detection @ 210 and 254 nm with no reference Using these HPLC conditions, starting material has a retention time of 3.30 min and product has a retention time of 4.05 min.

It was determined that removal of water produced by the dehydration reaction was important before performing the chlorination step. When ethanol is used as the solvent for this reaction, as in Example 1, the water is removed azeotropically upon removal of the ethanol. Several methods of drying the dichloromethane solution were attempted. Drying with MgSO$_4$ had a deleterious effect on the subsequent chlorination step, rendering the chlorination process very messy with a number of new impurities observed following HPLC analysis which were determined to be the corresponding chlorohydrins. On the other hand, a wash with brine was sufficient to remove enough water and had no deleterious effect on the chlorination step. Accordingly, the solution was stirred vigorously with brine (66 ml) for 30 minutes and then the phases were separated prior to chlorination step.

Step 2—Synthesis of 2-{4-[2-chloro-1,2-diphenylvinyl]phenoxy}-N,N-diethylethanamine (8)

The solution of 2-{4-[(Z)-1,2-diphenylvinyl]phenoxy}-N,N-diethylethanaminium hydrogen sulfate (7.94 grams) in methylene chloride obtained in step 1 is stirred at room temperature and treated with N-chlorosuccinimide (2.37 g, 17.7 mmol, 1.05 equivalents) in a single portion and left to stir at room temperature for 12 hours. The yellow solution became orange and then went back to yellow. After 12 hours, a sample was removed, concentrated and assayed by HPLC to confirm the extent of reaction. HPLC analysis revealed that the reaction had proceeded but not to completion. Accordingly, an additional 0.09 equivalents of N-chlorosuccinimide (203 mg, 1.52 mmol) was added and the solution stirred at room temperature for an additional 4 hours. The reaction was again assayed by HPLC which revealed that the reaction was near completion. Accordingly, an additional 0.09 equivalents of N-chlorosuccinimide (203 mg, 1.52 mmol) was added and the solution stirred for an additional 12 hours at room temperature. The reaction was again assayed by HPLC and an additional 0.058 equivalents of N-chlorosuccinimide (131 mg, 0.98 mmol) was added and the solution stirred for an additional 4 hours. HPLC indicated that the reaction was complete at that point. The reaction was carefully quenched by slow addition of 66 mL (600 mmol) of saturated aqueous sodium bicarbonate solution and the quenched mixture was stirred for 30 minutes at room temperature—the reaction mixture pH should be about 8-9 after addition of saturated aqueous sodium bicarbonate solution. The reaction yielded 6.86 grams of 2-{4-[2-chloro-1,2-diphenylvinyl]phenoxy}-N,N-diethylethanamine (8). The phases were separated and the organic phase was evaporated in vacuo. The resulting light brown oil was transferred to a tared amber bottle using a small volume of dichloromethane.

HPLC Conditions (Chlorination Step):
Sample preparation: Dissolve 1 mg/ml in mobile phase
Agilent 1100 HPLC
Phenomenex Jupiter-C4 250×4.6 mm 5 µm column
Solvent—54.85% Methanol, 44.85% Water, 0.3% triethylamine, pH adjusted to 2.5 by addition of 85% phosphoric acid
Flow rate—1.00 mL/min
Injection volume—10 µL
Gradient—30 min isocratic
UV detection @ 234 and 292 nm with no reference
Using these HPLC conditions, the retention time of product is 15 minutes.

Chromatographic Separation of Clomiphene Isomers

Clomiphene (mixture of isomers) in free base form obtained by steps 1 and 2 is loaded onto a chromatographic column (e.g. batch high pressure chromatography or moving bed chromatography) using the same solvent as used in steps 1 and 2 (here DCM) in order to separate the cis- and trans-clomiphene isomers. Trans-clomiphene is preferably eluted using a solvent suitable for recrystallization.

The invention claimed is:

1. A method for preparing clomiphene comprising dissolving a desired quantity of 1-{4-[2-(diethlamino)ethoxy]phenyl}-1,2-diphenylethanol in a suitable amount of a first solvent and therafter
    (a) adding to the solution sulfuric acid in an amount effective to dehydrate the 1-{4-[2-(diethylamino)ethoxy]phenyl}-1,2-diphenylethanol thereby producing a 2-{4-[(Z)-1,2-diphenylvinyl]phenoxy}-N,N-diethylethanaminium salt; and therafter
    (b) adding to the solution a chlorinating agent in an amount effective to chlorinate the diphenylvinyl]phenoxy}-N,N-diethylethanaminium salt thereby producing 2-{4-{2-chloro-1,2-1,2-diphenylvinyl]phenoxy}-N,N-diethletanamine,
    wherein the diphenylvinyl]phenoxy}-N,N-diethylethanaminium salt is not isolated prior to performing step (b).

2. The method of claim 1, wherein the first solvent is dichloromethane.

3. The method of claim 1, wherein the chlorinating agent in step (b) is N-chlorosuccinimide.

4. The method of claim 1, wherein the solution is maintained at a temperature of about 0° C. during addition of the sulfuric acid in step (a).

5. The method of claim 1, further comprising adding a suitable base to the clomiphene solution obtained in step (b) thereby converting clomiphene to the free base form.

6. The method of claim 5, wherein the suitable base is saturated aqueous sodium bicarbonate solution).

7. The method of claim 5, further comprising loading the solution comprising clomiphene free base onto a chromatographic column and eluting the column under conditions suitable for obtaining trans-clomiphene.

8. The method of claim 7, further comprising recrystallizing the trans-clomiphene.

9. The method of claim 1, further comprising
    (c) dissolving the 2-{4-[2-chloro-1,2-diphenylvinyl]phenoxy}-N,N-diethyl ethanamine produced in step (b) in a suitable second solvent and an amount of racemic binaphthyl-phosphoric acid (BPA) effective to react with the 2-{4-[2-chloro-1,2-diphenylvinyl]phenoxy}-N,N-diethyl ethanamine thereby producing a trans-clomiphene-BPA salt.

10. The method of claim 9, wherein the second solvent in step (c) is methanol.

11. The method of claim 9, further comprising the steps of
    (d) extracting the trans-clomiphene-BPA salt obtained in step (c) in a suitable third solvent and a basic aqueous solution to produce the trans-clomiphene free base; and
    (e) adding to the solution obtained in step (d) an amount of citric acid effective to produce trans-clomiphene citrate.

12. The method of claim 11, wherein the basic aqueous solution in step (d) is an NH$_3$ solution.

13. The method of claim 9, wherein the second solvent in step (c) is ethyl ether or ethyl acetate.

14. The method of claim 11, wherein the second suitable organic solvent is ethyl ether or ethyl acetate.

15. The method of claim 9, wherein the first solvent is dichloromethane.

16. The method of claim 9, wherein the chlorinating agent in step (b) is N-chlorosuccinimide.

* * * * *